United States Patent
Wagner et al.

(10) Patent No.: US 7,204,836 B2
(45) Date of Patent: Apr. 17, 2007

(54) INSTRUMENT FOR MINIMAL INVASIVE SURGERY

(75) Inventors: Carl-Sebastian Wagner, Bretten (DE); Andreas Dingler, Birkenfeld (DE); Josef Bartolić, Karlsruhe-Grötzingen (DE)

(73) Assignee: Richard Wolf GmbH, Knittlingen (DE)

( * ) Notice: Subject to any disclaimer, the term of this patent is extended or adjusted under 35 U.S.C. 154(b) by 294 days.

(21) Appl. No.: 10/635,338

(22) Filed: Aug. 6, 2003

(65) Prior Publication Data

US 2004/0098041 A1 May 20, 2004

(30) Foreign Application Priority Data

Aug. 7, 2002 (DE) ................. 102 36 070

(51) Int. Cl.
*A61B 18/18* (2006.01)

(52) U.S. Cl. .......................... 606/51; 606/205

(58) Field of Classification Search .......... 606/45–50, 606/51, 52, 205–207, 210, 174, 27, 41; 600/104; 81/347, 353, 354
See application file for complete search history.

(56) References Cited

U.S. PATENT DOCUMENTS

| 5,290,309 | A | | 3/1994 | Kothe |
| 5,389,104 | A | | 2/1995 | Hahnen et al. |
| 5,478,350 | A | | 12/1995 | Kratsch et al. |
| 5,490,861 | A | * | 2/1996 | Kratsch et al. ............. 606/205 |
| 5,496,317 | A | * | 3/1996 | Goble et al. ................. 606/48 |
| 5,499,998 | A | * | 3/1996 | Meade ....................... 606/207 |
| 6,451,018 | B1 | * | 9/2002 | Lands et al. ................. 606/50 |

FOREIGN PATENT DOCUMENTS

| DE | 39 21 935 A1 | 2/1990 |
| DE | 44 96 959 T1 | 9/1996 |
| DE | 197 28 114 C1 | 2/1999 |
| DE | 197 34 781 A1 | 2/1999 |

* cited by examiner

*Primary Examiner*—Michael Peffley
*Assistant Examiner*—Pete Vrettakos
(74) *Attorney, Agent, or Firm*—Akin Gump Strauss Hauer & Feld, LLP (57) ABSTRACT

A medical forceps has a forceps shank and a forceps jaw which comprises at least one movable jaw part, wherein the jaw part has a curved linkage arm at its proximal end. The linkage arm is movably guided in a curved guide path of an insert which is inserted into at least one receiver at the distal end of the forceps shank.

15 Claims, 9 Drawing Sheets

INSTRUMENT FOR MINIMAL INVASIVE SURGERY

BACKGROUND OF THE INVENTION

The invention relates to a medical forceps, in particular for minimal invasive surgery.

From German published patent application DE 197 34 781 A1, for example, there is known a bipolar gripping forceps for minimal invasive surgery. With this forceps the jaw parts of the forceps jaw are opened and closed via toggle lever elements by way of moving an actuation rod arranged in the inside of the forceps shank. In order to insulate those parts of the jaw part conducting current these parts have an insulation coating. The disadvantage of these coatings is the fact that they must have a certain layer thickness in order to ensure adequate insulation properties. At the same time it is disadvantageous that the layer thickness on the surfaces is, for example, thicker than at the edges. Furthermore, due to the relatively thick insulation layers the wall thickness of the individual parts consisting of metal must be reduced, by which means the stability is reduced to a considerable extent. Furthermore, the toggle lever mechanics are complicated in manufacture and assembly.

BRIEF SUMMARY OF THE INVENTION

It is therefore the object of the invention to provide a medical forceps which is simpler to manufacture and permits a simpler insulation of the parts conducting current.

This object is achieved by a medical forceps comprising a forceps shank and a forceps jaw having at least one movable jaw part, wherein the jaw part comprises at its proximal end a curved linkage arm which is movably guided in a curved guide path of an insert, and wherein the insert is inserted into at least one receptacle at a distal end of the forceps shank. Advantageous embodiments are described below and in the dependent claims.

The forceps according to the invention comprises a forceps shank and a forceps jaw arranged at the distal end of the forceps shank. The forceps jaw comprises at least one movable jaw part. The movable jaw part comprises a curved linkage arm at its proximal end, which is rigidly connected to the jaw part. The curved linkage arm is movably guided in a curved guide path at the distal end of the forceps shank in the direction of the guide path. Due to the circular arc-shaped curvature of the guide path and the corresponding curvature of the curved linkage arm, at the same time with a movement of the linkage arm in the guide path one achieves a deflection of the movable jaw part. The jaw part and the guide path are curved outwardly in the distal direction. This means that the tangential extension of the distal end of the guide path extends inclined to the longitudinal axis of the forceps shank. This course of the guide path and the corresponding curvature of the linkage arm have the effect that on movement of the linkage arm in the guide path the jaw part connected to the linkage arm is changed in its angular position with respect to the longitudinal axis of the forceps shank, so that the jaw part may be opened and closed. The guide path is formed in an insert which is preferably fittingly applied in at least one corresponding recess or receptacle at the distal end of the forceps shank. The design according to the invention is considerably simpler in its construction than known toggle lever systems, since the number of individual parts required is significantly lower. This reduces the manufacturing and assembly cost. Since for each movable jaw part there are provided individual mechanics which are independent of the other moving parts, consisting of the linkage arm and the guide path, with the design according to the invention it is more simply possible to electrically insulate the movable jaw parts with respect to one another. Generally, the forceps jaw may be designed in various manners, for example as a gripping forceps, as a scissors or as a monopolar or bipolar coagulation instrument. The linkage of the movable jaw part according to the invention is basically suitable for every conceivable design of the distal end of the jaw part. The invention may thus be applied in a larger number of different instruments.

Advantageously, the insert with the guide path is applied into the corresponding receptacle or receiver from the distal end of the forceps shank. This means that all elements required for the deflection or mounting of the jaw parts may be very simply inserted in the forceps shank from the distal end. This permits a simple assembly. Furthermore, the insulation elements may be simply inserted between the individual components.

At the proximal end of the linkage arm there preferably engages an actuation rod which is axially movably arranged for moving the connected jaw part in the forceps shank. At its proximal end the actuation rod is connected, for example, in the known manner to the forceps handle. Preferably the distal end of the actuation rod is directly connected to the proximal end of the linkage arm and at its opposing end is connected to the distal end of the actuation rod in an articulated manner. The articulated connection may, for example, be formed by a rivet or bolt. Alternatively, for example a pliant material may be used for the actuation rod. If the actuation rod is moved distally, the curved linkage arm in the guide path is likewise moved distally by which means, due to the curvature, the jaw part connected to the linkage arm is pivoted outwardly so that the forceps jaw is opened. The actuation rod is retracted for closing the forceps jaw, by which means the linkage arm in the guide path is moved proximally and the movable jaw part is again pivoted towards the longitudinal axis of the forceps shank. If the guide paths and the linkage arms are arranged such that they are curved in the distal direction towards the longitudinal axis of the forceps shank, one may create a forceps jaw which is closed on distal movement of the actuation rod and is opened on proximal movement of the actuation rod.

It is particularly preferred to provide two movable jaw parts which in each case at their proximal ends comprise a curved linkage arm which in each case is guided in an associated curved guide path in at least one insert in the direction of the guide paths, wherein the two linkage arms and the associated guide paths are curved mirror imaged or opposed to one another. If the guide paths and linkage arms are curved such that their tangential extensions in the distal direction move away from the longitudinal axis of the forceps shank, one then creates a forceps jaw with two movable jaw parts which may be opened by the distal movement of an actuation rod. If the guide paths and the linkage arms are curved in the reverse direction, i.e., are curved in the distal direction towards the longitudinal axis of the forceps shank, one may create a forceps jaw which is closed on distal movement of the actuation rod. The jaw parts, according to the purpose of application, may be designed as scissor elements, gripping elements or in any other forms. Preferably, the two guide paths and the two linkage arms are in each case arranged mirror images of one another, i.e., they have the same radii of curvature and are curved in opposing directions. In this manner, one may achieve a symmetrical opening and closing of the forceps jaw. The guide paths are formed in at least one insert which, as described above, may be applied at the distal end of a forceps jaw into a corresponding recess. This permits a simple assembly of the forceps jaw on the forceps shank since the jaw parts may be simply inserted with the insert into the receiver on the forceps shank.

The linkage arms and the associated guide paths are preferably each curved in a plane, and the planes of curvature of the two linkage arms preferably extend parallel to one another. Accordingly, the jaw parts connecting to the linkage arms may be closed and opened in one plane.

With a particular embodiment the jaw part and the associated linkage arm are designed electrically conducting. This permits the application of the forceps according to the invention as a coagulation instrument.

The guide paths are preferably each formed as a groove in at least one insert, wherein the groove faces the longitudinal axis of the forceps shank. The insert at the same time preferably forms a semi-shell element which has a cross sectional shape corresponding essentially to half the cross section of the forceps shank or its inner space. The guide paths may thus be arranged very close to the longitudinal axis of the forceps shank so that, in particular, one may create a very slim instrument.

Preferably, there are provided two inserts or semi-shell elements which are arranged such that their surfaces in which the guide paths are formed face one another. The two inserts arranged parallel to the longitudinal axis of the forceps shank may be rigidly connected to one another, for example by way of pins or rivets. The linkage arms of the two jaw parts are guided between the two inserts in the respective guide paths. This has the effect that the linkage arms in a direction transverse to the longitudinal axis of the forceps jaw lie very close to one another so that a compact design and good force transmission are possible.

It is furthermore preferred for the two assembled inserts in cross section to have an outer contour, which corresponds to the shape of the inner cross section of the forceps shank, and to be applied into the forceps shank from the distal end. This permits a simple and inexpensive assembly since only a few components are necessary. The two inserts in the form of semi-shell elements are held together by the surrounding forceps shank or by additional holding elements. Furthermore, in this manner one ensures a smooth outer contour of the forceps shank which is easy to clean.

The inserts preferably comprise locking elements which are in engagement with corresponding locking elements on the forceps shank. For example, locking projections may be formed on the inserts at their proximal end, which engage into corresponding recesses on the forceps shank. In this manner, inserts with the jaw parts arranged thereon may be fixed on the forceps shank with a positive fit. For the purposes of cleaning and maintenance the jaw parts may further be easily separated again from the forceps shank by releasing the locking elements. It is conversely also possible, for example, to provide locking recesses on the insert and corresponding locking projections on the forceps shank.

According to a preferred embodiment, two inserts or semi-shell elements are provided with an insulation element arranged between them. The insulation element is preferably designed as a flat disk, for example of plastic or ceramic, and extends parallel to the longitudinal axis of the forceps shank. By way of such an insulation element the two inserts and the jaw parts arranged therein may be very simply electrically insulated with respect to one another. Since the pivot mechanics consisting of the linkage arm and the guide groove are formed for each jaw part separately in one of the two inserts, this electrical insulation is possible by way of a single insulation element between the two inserts.

Alternatively or additionally, the inserts may be applied into an insulation element at the distal end of the forceps shank. At the same time, the inserts are applied into receptacles or receivers which are formed in the insulation element. The insulation element for its part is arranged at the distal end, i.e., preferably in the distal end of the forceps shank. Such an insulation element may, for example, be formed of plastic or ceramics and comprise two recesses open towards the distal end into which the inserts may be fittingly inserted. Such an insulation element additionally permits an electrical insulation with respect to the forceps shank. The inserts may, for example, be held in the insulation element by locking means. Furthermore, the insulation also comprises preferably locking elements via which the insulation element is releasable connected to the forceps shank. The insulation element at the same time is preferably applied into the forceps shank from the distal end.

According to an alternative embodiment, the guide path is formed as a groove on the outer side of an insert, which is inserted into a central receptacle or recess arranged at the distal end of the forceps shank, so that the groove is spaced from the longitudinal axis the forceps shank. This means the groove is arranged exactly in reverse to the embodiment with the semi-shell elements. At the distal end of the forceps shank there is preferably formed a fitting recess into which the insert may be inserted in a fitting manner. On the recess there are preferably formed locking elements in order to releasably fix the insert in the forceps shank.

Preferably, with this embodiment, there are formed two guide paths on two opposing sides of the insert. Thus only a single component is required in which both guide paths are formed for two movable jaw paths. In this manner, the number of required components may be reduced further.

The guide paths may be formed in one insulation element. For example, the insert or inserts may be formed as an insulation element, for example of plastic or ceramic. This design permits further insulation elements to be done away with in order to electrically insulate both jaw parts with respect to one another or to electrically insulate one or both jaw parts with respect to the forceps shank. Thus, a very effective electrical insulation of these components may be created.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
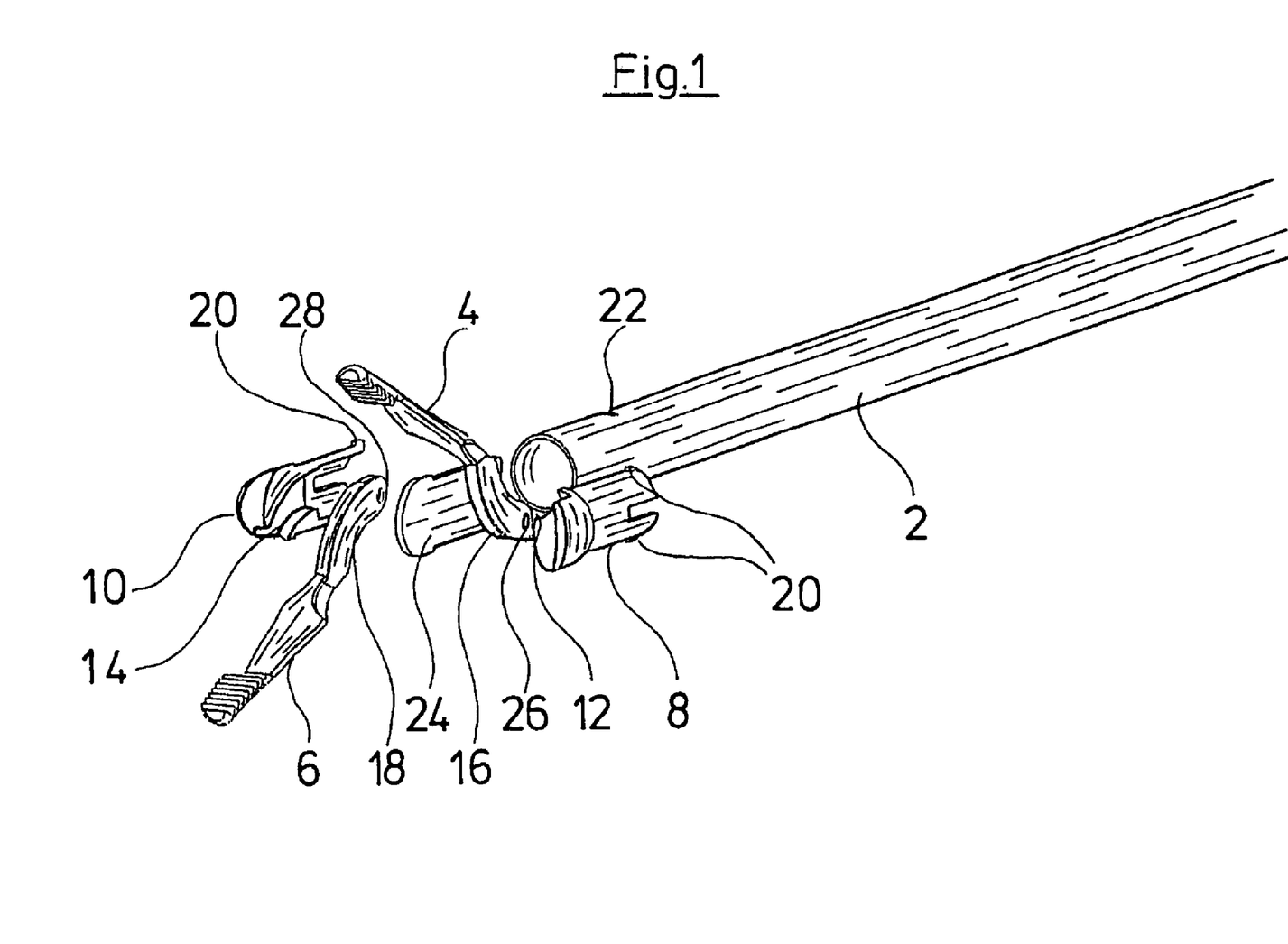
FIG. 1 is an exploded view of the distal end of the forceps according to a first embodiment of the invention.

FIG. 1 shows an exploded view of the distal end of a forceps according to a first embodiment of the invention. The shown embodiment is a medical forceps designed as a bipolar coagulation gripping forceps. The forceps comprises a forceps shank 2 on whose distal end there is formed a forceps jaw, consisting of two movable jaw parts 4 and 6. The branches or jaw parts 4, 6 are movably guided in two inserts in the form of semi-shell elements 8 and 10. The distal ends of the jaw parts 4 and 6 may be designed in various manners. In the shown example they have serrated gripping surfaces. Alternatively, the jaw parts may also be designed as scissors. The proximal ends of the jaw parts 4, 6 are designed as linkage arms 16 and 18. The linkage arms 16 and 18 are curved in a circular arc shape. In the semi-shell elements 8 and 10 there are formed guide paths 12 and 14 in the form of grooves curved in a circular arc-shaped manner. The curvature of the guide paths 12, 14 corresponds to the arc shape of the linkage arms 16 and 18, so that the linkage arms 16 and 18 may be slidingly guided in the respective guide paths 12 and 14.

The semi-shell elements 8 and 10 in each case have an essentially semicircular cross section, so that the two semi-shell elements 8 and 10 together form a cylindrical receiving part which may be inserted into the distal end of the forceps shank 2 in the longitudinal direction of the forceps shank 2. The inside of the distal end of the forceps shank 2 at the same time forms a receptacle or receiver for the semi-shell elements 8 and 10. At the same time, the semi-shell elements 8, 10 with their surfaces facing one another extend parallel to the longitudinal axis of the forceps shank 2. With this, the guide paths 12 and 14 are formed in the planar surfaces of the semi-shell elements 8 and 10 which face one another. At their proximal end the semi-shell elements 8 and 10 comprise resilient locking projections 20. If the semi-shell elements are inserted into the distal end of the forceps shank 2, these locking projections 20 may come into engagement with two recesses 22 formed diametrically opposed to one another in the forceps shank. Additionally, the semi-shell elements 8 and 10 may be connected to one another by way of further connection elements, for example pins or rivets, or may be adhered to one another.

Between the two semi-shell elements 8 and 10 and the linkage arms 16 and 18 guided in their guide paths 12 and 14 there is arranged an insulation element 24 in the form of a flat insulation plate, for example of plastic or ceramic. The insulation element 24 extends parallel to the longitudinal axis of the forceps shank 2 and ensures an electrical insulation between the two semi-shell elements 8 and 10 and the associated jaw parts 4 and 6. This permits the two jaw parts 4 and 6 to be impinged with differing polarities for use as a bipolar coagulation forceps. At the same time, the electrical insulation between the two jaw parts 4 and 6 is very simple since only a single insulation element 24 is required.

At its proximal end the linkage arms 16 and 18 have through-bores 26 and 28 for the articulated connection to actuation rods (not shown in FIG. 1). The bores 26 and 28 extend transversely to the longitudinal axis of the forceps shank and to the movement plane of the jaw parts 4 and 6. Additionally, the proximal ends of the linkage arms 16 and 18 are slotted in a plane normal to the bores 26 and 28. The distal ends of the actuation rods engage into these slots and are articulatably held at the respective bore 26, 28 by a pin or bolt. By way of axial movement of the actuation rods in the inside of the forceps shank 2 it is then possible to displace the linkage arms in the guide paths 12, 14 in the direction of the guide paths 12, 14, wherein the jaw parts 4 and 6 are moved towards one another or away from one another.

Figure 2:
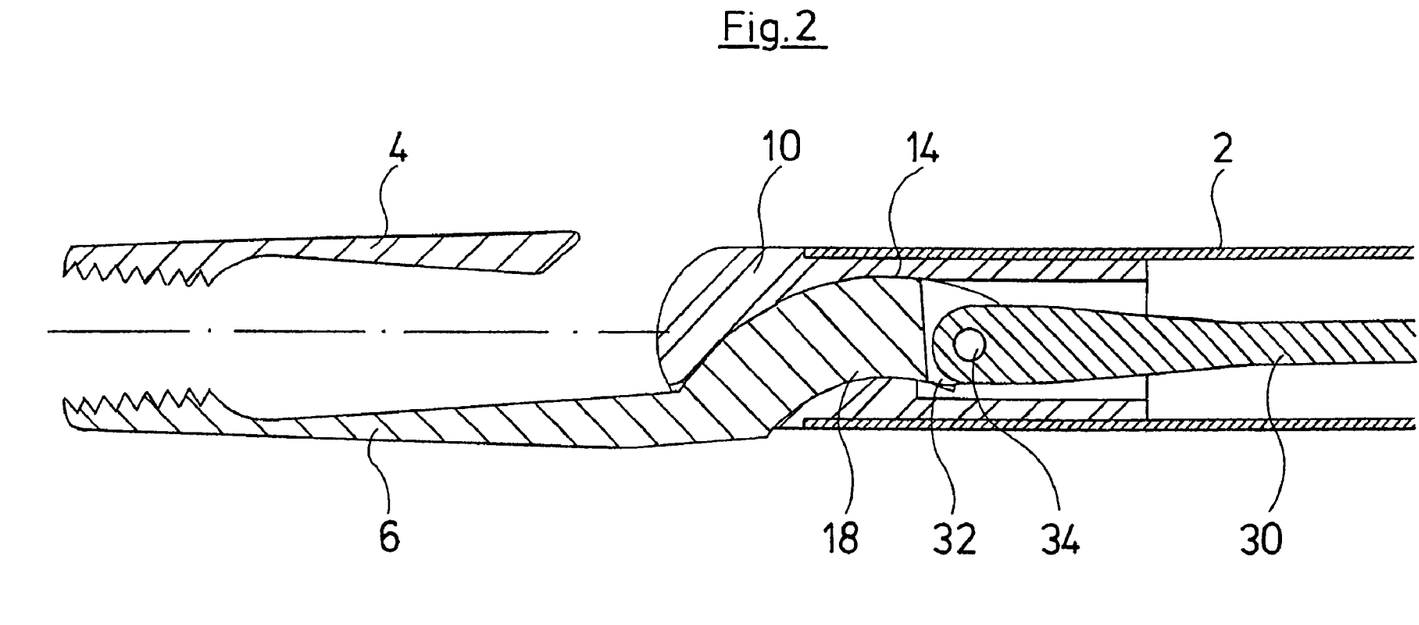
FIG. 2 is a sectional view of the distal end of the forceps according to FIG. 1.

This is explained in more detail by way of FIG. 2 which shows a longitudinal section of the assembled forceps jaw according to FIG. 1. In the assembled condition the semi-shell elements 8 and 10 are applied in the forceps shank 2 from the distal end. On the outer circumference of the semi-shell elements 8, 10 there is formed a shoulder so that a stepless transition from the distal end of the semi-shell elements 8, 10 to the outer circumference of the forceps shank 2 is ensured. In the inside of the forceps shank 2 there is arranged an actuation rod 30 whose distal end is flattened in a manner such that it may engage into the slot 32 at the proximal end of the linkage arm 18. In this position it is connected to the linkage arm 18 via the pin 34 in an articulated manner.

The guide path 14 is curved in a circular arc-shaped manner, wherein the curvature runs such that it moves away from the longitudinal axis X of the forceps shank 2 in the distal direction so that the tangential extension of the distal end of the circular arc runs at an acute angle to the longitudinal axis X. The linkage arm 18 is curved according to the guide path 14 so that it may be slidingly guided in the guide path 14. For opening the forceps jaw, the actuation rod 30 is moved distally, by which means the linkage arm 18 in the guide path 14 is likewise moved distally. On account of the curvature of the guide path 14 and of the linkage arm 18 at the same time the jaw part 6 is deflected or pivoted outwardly, i.e. the forceps jaw consisting of the jaw parts 4 and 6 opens. The movement of the forceps jaw 4 is effected in a corresponding manner, wherein the guide path 12 and the linkage arm 16 of the jaw part 4 are curved exactly reversely to the linkage arm 18 and the guide path 14, so that the jaw part 4 may also be pivoted outwardly with a distal movement of the actuation rod. The two linkage arms 16 and 18 may be connected to the same actuation rod 30. Alternatively, one may provide two actuation rods which in particular may be applied with a bipolar coagulation gripping forceps wherein the actuation rods simultaneously serve the conduction of the voltage to the jaw parts 4 and 6.

Figure 3:
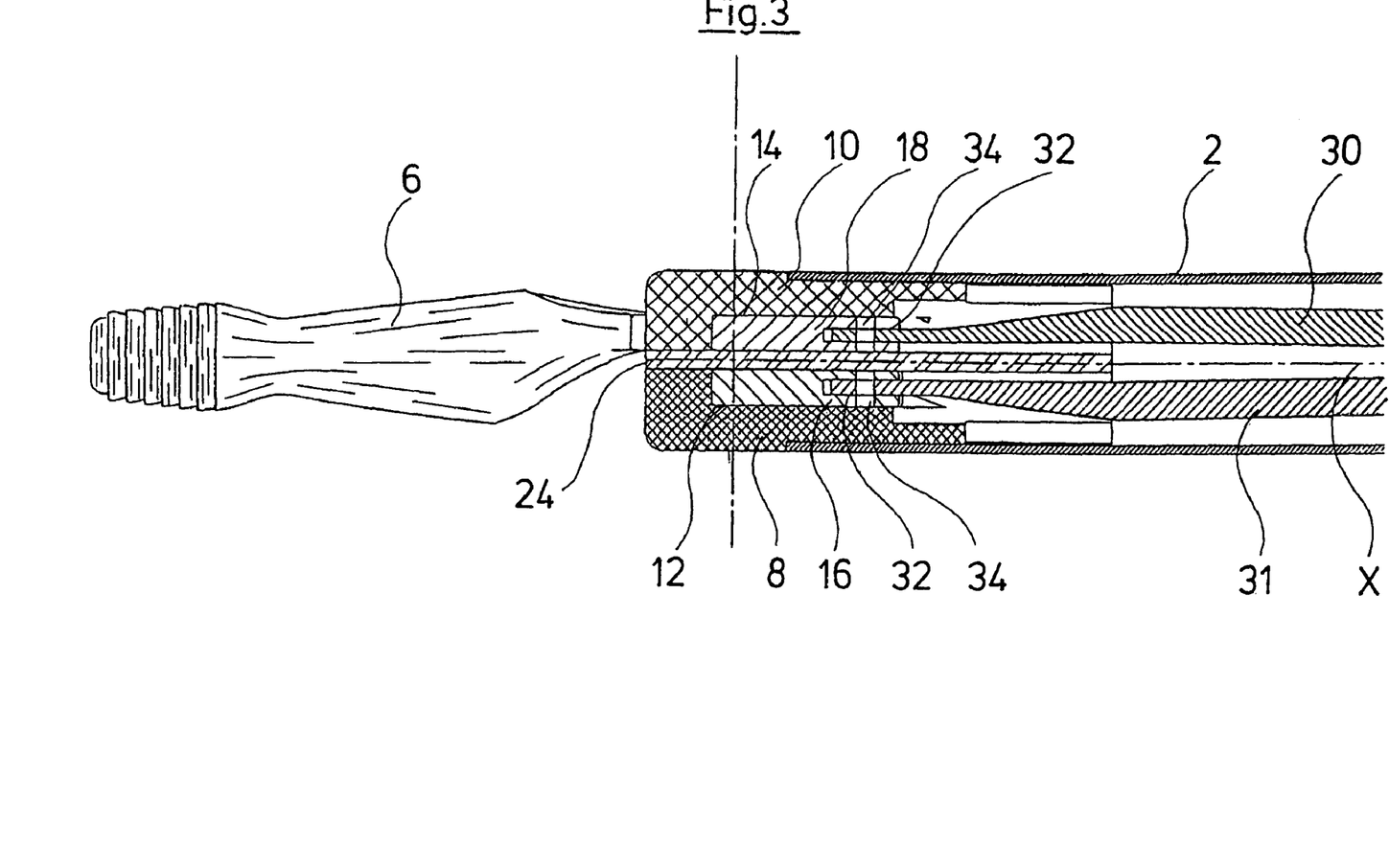
FIG. 3 is a further sectional view of the distal end according to FIGS. 1 and 2.

FIG. 3 shows a section through the assembled forceps jaw normal to the section plane of FIG. 2. In FIG. 3 it may be recognized how the two semi-shell elements 8 and 10 with the insulation element 24 lying therebetween may be completed into a circularly cylindrical receiving element which is applied from the distal end into the forceps shank 2 in its longitudinal direction X. The two semi-shell elements 8 and 10 with the inserted linkage arms 16 and 18 are completely electrically separated from one another by the insulation element 24. The two linkage arms 16 and 18 in the guide paths 12 and 14 extend in planes parallel to one another, so that the two jaw parts 4 and 6 may be pivoted towards one another in a common opening plane. The jaw part 6 protrudes with respect to the linkage arm 18 to the longitudinal axis X. Accordingly, conversely the jaw part 4 (not shown in FIG. 3) projects with respect to the associated linkage arm 16 to the longitudinal axis X, so that the two jaw parts 4 and 6 come to lie over one another. The two jaw parts 4 and 6 as well as the semi-shell elements 8 and 10 may be formed identically, by which means the number of required parts is reduced. With the bipolar coagulation gripping forceps according to FIG. 3 in the inside of the forceps shank 2 there are provided two actuation rods 30 and 31 extending parallel to the longitudinal axis X. The actuation rods 30 and 31 are formed flattened at their distal ends so that they may engage into the slots 32 on the linkage arms 16 and 18 and here may be held in an articulated manner by the pins 34. The actuation rods 30 and 31 at their regions connecting to the distal ends are electrically insulated, so that they may serve for voltage supply of the jaw parts 4 and 6. It is thus possible to apply a voltage between the jaw parts 4 and 6. The actuation rods 30 and 31 may also be grouped together in a common actuation rod, in particular both actuation rods 30 and 31 may be arranged in a common insulation.

Figure 4:
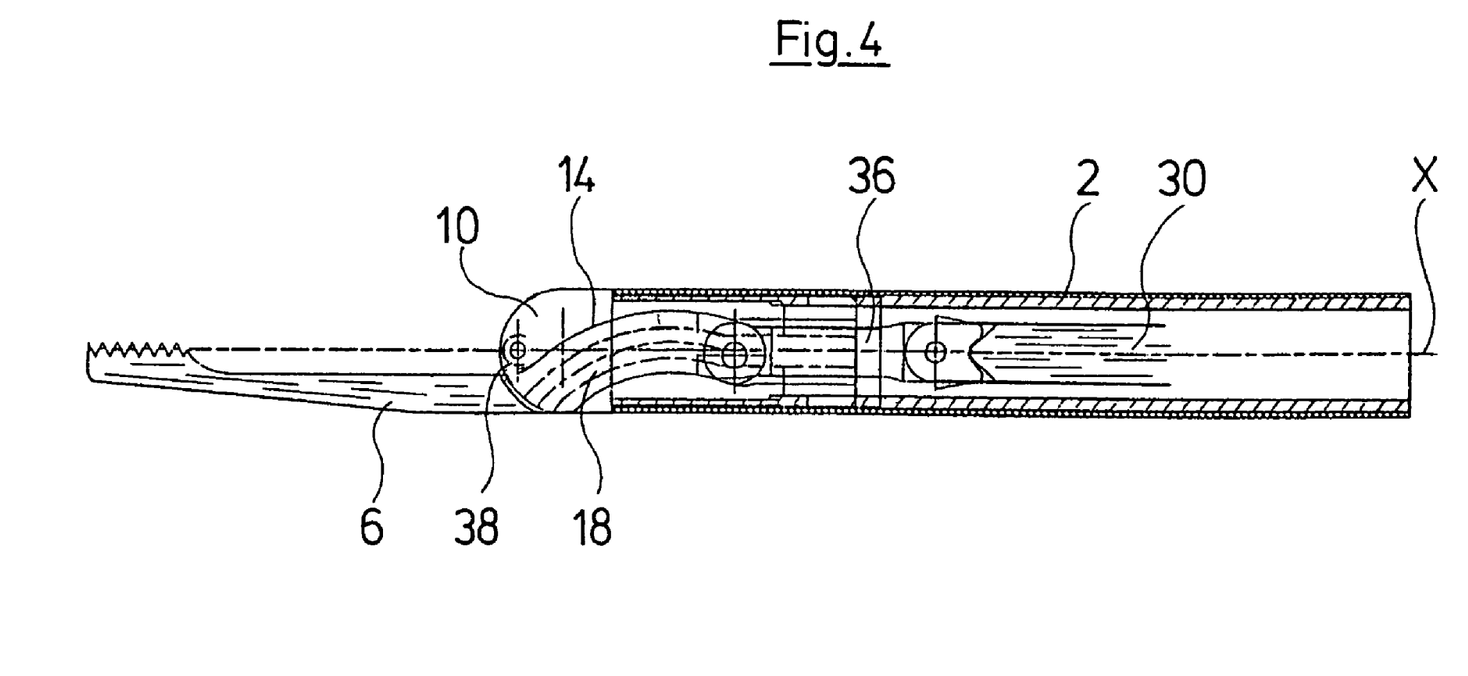
FIG. 4 is a partly sectional view of the distal end of the forceps according to an alternative embodiment of the invention.

FIG. 4 shows a sectional view similar to FIG. 2 according to a modified embodiment. The embodiment according to FIG. 4 corresponds essentially to the embodiment explained by way of FIG. 2 with the difference that the linkage arm 18 is connected to the distal end of the actuation rod 30 via an additional linkage element 36. The linkage element 36 is fastened to the distal end of the actuation rod 30 in an articulated manner. With its opposing end the linkage element 36 is connected in an articulated manner to the proximal end of the linkage arm 18. At the same time, the two pivot axes extend parallel to one another and normal to the longitudinal axis X. For the second jaw part 4 (not shown here) there is provided a second linkage element 36 which connects the proximal end of the linkage arm 16 to the same actuation rod 30. This design is suitable for a monopolar coagulation forceps which is shown in FIG. 4. With such a forceps the forceps shank on its outer side is additionally provided with an insulation layer. The semi-shell element 10 shown in FIG. 4 at its distal end additionally comprises a bore 38 in which, for example, a pin is inserted in order to connect the semi-shell element 10 to the semi-shell element 8. The design and manner of functioning of the forceps jaw according to FIG. 4 corresponds to that forceps jaw explained by way of FIGS. 1 and 3.

Figure 5:
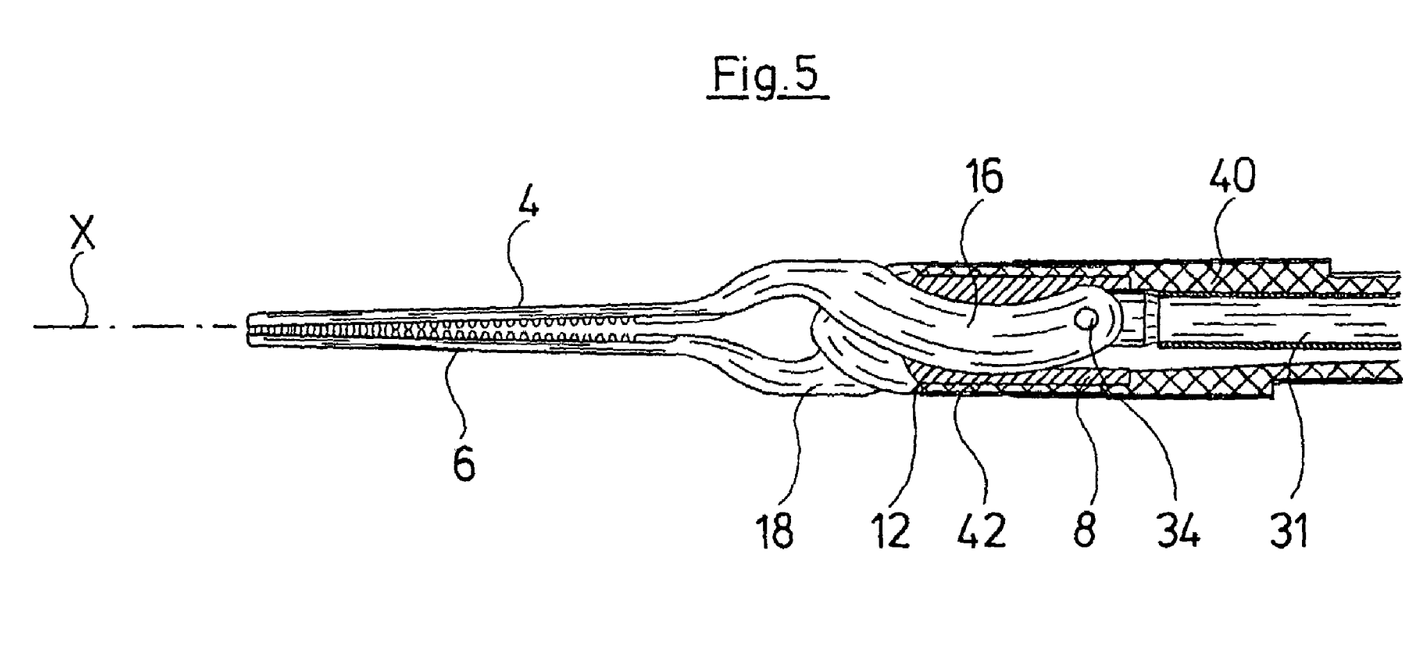
FIG. 5 is a sectional view of the distal end of the forceps according to a further alternative embodiment.

FIG. 5 shows a sectional view similar to FIGS. 2 and 4 of a forceps jaw according to a further embodiment. Disregarding the different design of the jaw parts 4 and 6, the forceps shown in FIG. 5 differs from the forceps described up to now in that the semi-shell elements 8 and 10 are applied into a common insulation body 40. The insulation body 40 is formed essentially circularly cylindrical and at its distal end comprises two recesses 42 which serve as receptacles or receivers and into which the semi-shells 8 and 10 are fittingly inserted from the distal end. Since the semi-shell elements 8 and 10 are applied into different recesses 42, they are electrically separated from one another. The actuation rods 30 and 31 are connected to the linkage arms 16 and 18 as described previously. The movement of the linkage arms 16 and 18, and thus of the jaw parts 4 and 6 on movement of the actuation rods 30 and 31, corresponds to the manner of functioning described by way of FIGS. 1 to 4.

Figure 6:
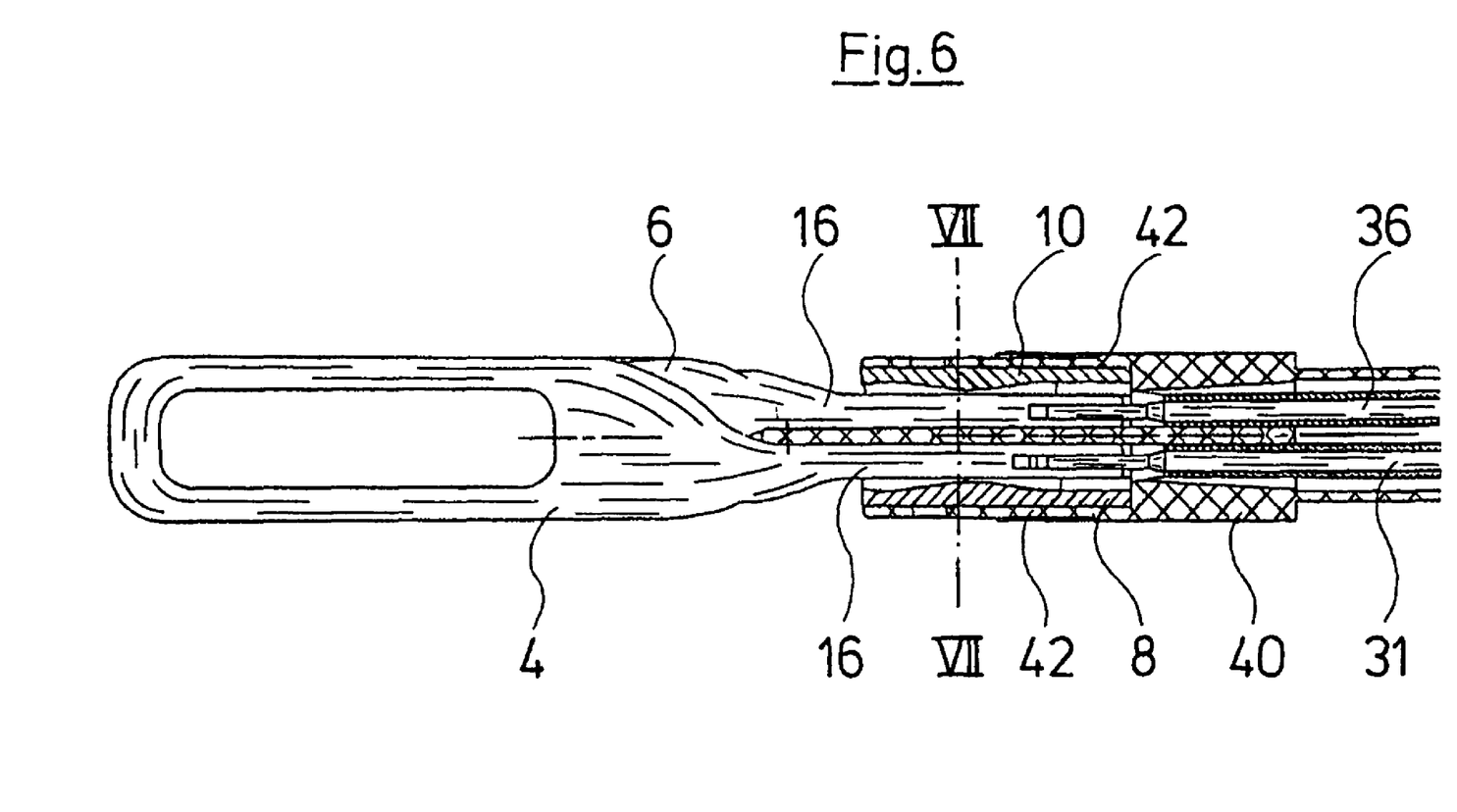
FIG. 6 is a further sectional view of the forceps according to FIG. 5.

FIG. 6 shows a sectional view of the forceps jaw according to FIG. 5 in a section plane normal to the section plane according to FIG. 5. In FIG. 6 one may recognize that the two semi-shell elements 8 and 10 are applied electrically separated from one another into two recesses 42 at the distal end of the insulation body 40. The semi-shell elements 8 and 10 may be held in the recesses with a friction, positive or material fit. One may, for example, provide locking means or the semi-shell elements 8 and 10 may be adhered into the recesses 42. The insulation body 40 is applied into a forceps shank 2 (not shown in FIG. 6) from the distal end. Here, for example, it may be held by locking means according to the design according to FIG. 1. The actuation rods 30 and 31 are coated with an insulation layer. In this manner the jaw parts 4 and 6 are completely electrically separated from one another so that one may apply a voltage between them.

Figure 7:
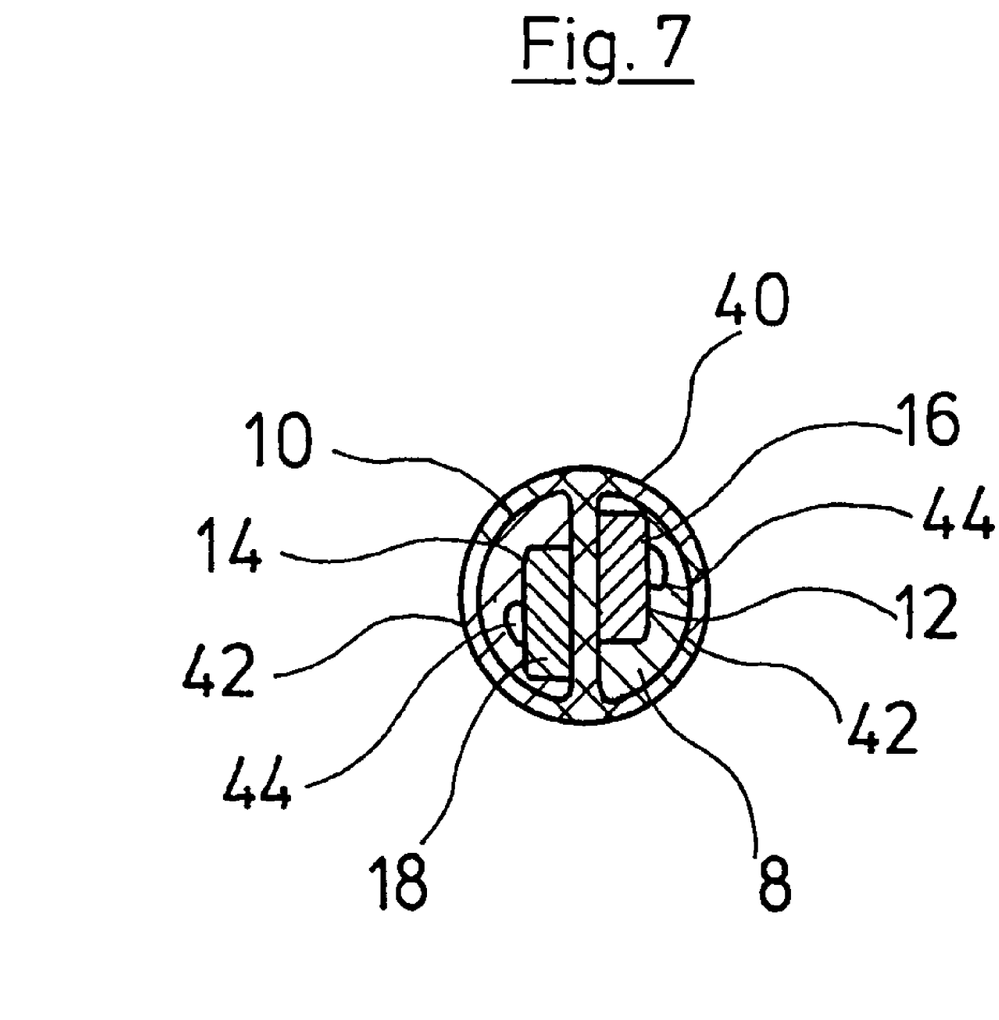
FIG. 7 is a sectional view along line VII—VII in FIG. 6.

FIG. 7 shows a sectional view along the line VII—VII in FIG. 6. In FIG. 7 one may also see the separate arrangement of the semi-shell elements 8 and 10 in the recesses or chambers 42. One may additionally recognize than in the guide paths 12 and 14 there are additionally provided grooves 44 which extend in the guide paths 12 and 14 over their whole length. These grooves permit a rinsing-through of the forceps even in the assembled condition.

Figure 8:
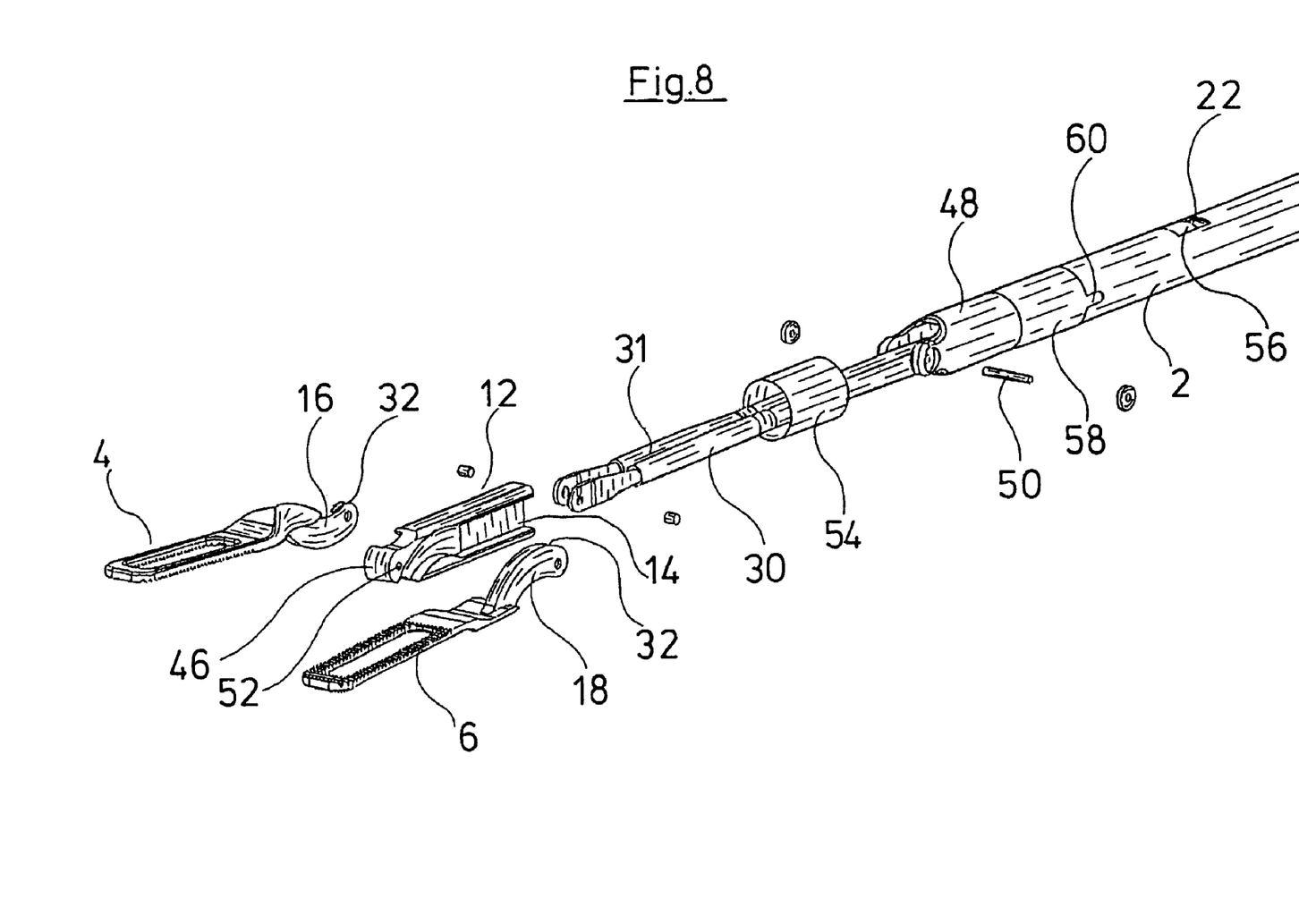
FIG. 8 is an exploded view of the distal end of a forceps according to a further embodiment.

FIG. 8 shows an exploded view of a forceps jaw according to a further embodiment of the invention. In contrast to the previously described embodiments, in the embodiment according to FIG. 8 the guide paths 12 and 14 are not formed in two semi-shell elements but in a common insert in the form of a receiving part 46. The receiving part 46 has the shape of a double T-carrier, i.e., the guide paths 12 and 14 are in the form of grooves at two opposing outside surfaces extending parallel to one another and which extend parallel to the longitudinal axis X of the forceps shank 2. The design of the jaw parts 4 and 6 with the linkage arms 16 and 18 connecting to the proximal end corresponds to the design described by way of the previous Figures. The circular arc-shaped curvature of the guide paths 12 and 14 is designed according to the FIGS. 1 to 7. In the forceps shank 2 there are provided two actuation rods 30 and 31 which, as previously described, engage into the slots 32 of the linkage arms 16 and 18 and here are linkedly fastened via pins. The receiving part 46 is manufactured of an insulating material, such as plastic or ceramic, and the actuation rods 30 and 31 are likewise electrically insulated. In this manner, one achieves an electrical separation between the jaw parts 4 and 6, so that a voltage may be applied between these. The receiving part 46 from the distal end is applied into a second receiving part 48, which is likewise formed electrically insulating and which has a corresponding recess or receiver. Here, it is secured by a pin 50 which extends through the bores at the distal end of the second receiving part 46. For increasing the mechanical stability via the second receiving part 48 one further inserts a metal cylinder sleeve 54. The second receiving part 48 is applied from the distal end into the forceps shank 2 and is secured by locking projections 56 in the recess 22. The locking projection 56 is formed elastically at the proximal end of the second receiving part 48, so that the second receiving part 48 may be released from the forceps shank for the purposes of repair and cleaning.

A second sleeve 58 is pushed on at the proximal end of the second receiving part 48, and laterally comprises two lugs 60 which engage into corresponding recesses on the forceps shank 2. The metallic sleeves 54 and 58 are adhered to the second receiving part 48. The lugs 60 may thus serve as a rotation securement of the second receiving part 48, and of the forceps jaw connected to this, with respect to the forceps shank 2.

Figure 9:
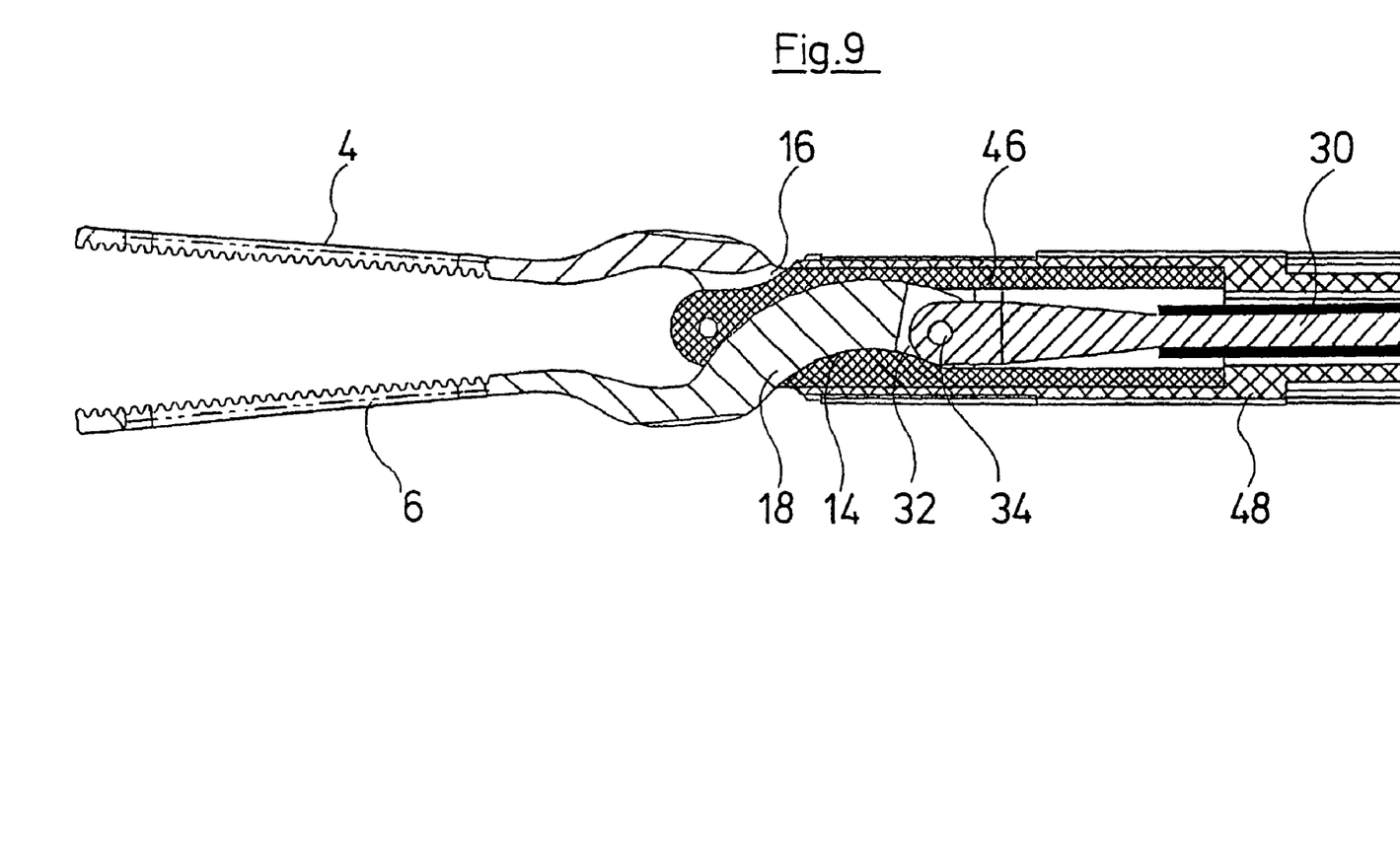
FIG. 9 is a sectional view of the forceps according to FIG. 8.

FIG. 9 shows a longitudinal section through the assembled forceps jaw according to FIG. 8. As with the previously described embodiments, the linkage arms 16 and 18 of the jaw parts 4 and 6 are slidingly movably guided in the guide paths 12 and 14 in the longitudinal direction of the guide paths 12 and 14. At the proximal end, the linkage arms 16 and 18 are connected to the actuation rods 30 and 31 in an articulated manner. If the actuation rods 30 and 31 are moved distally, the linkage arms 16 and 18 are pulled out of the guide paths 12 and 14 in the distal direction, wherein the jaw parts 4 and 6 are pivoted apart. As with the previous embodiment, the jaw parts 4 and 6 at the same time pivot about a virtual linkage point situated outside the forceps jaw. Apart from the already explained advantages this permits an improved force transmission.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A medical forceps comprising a forceps shank (2) and a forceps jaw having at least one movable jaw part (4, 6), wherein the at least one movable jaw part (4, 6) comprises at its proximal end a linkage arm (16, 18) guided to be movable longitudinally in a curved guide path (12, 14) of an insert, the curved guide path having a form of a groove having a flat, planar bottom and curved side walls, the side walls being curved laterally of the groove in a circular arc shape corresponding to the circular arc shape of the linkage arm, wherein the insert (8, 10; 46) is inserted into at least one receptacle at a distal end of the forceps shank (2).

2. The medical forceps according to claim 1, wherein the insert (8, 10; 46) is applied into the receptacle from the distal end of the forceps shank (2).

3. The medical forceps according to claim 1, wherein at a proximal end of the linkage arm (16, 18) there engages an actuation rod (30, 31) which is arranged to be axially movable for moving the at least one moveable jaw part (4, 6) in the forceps shank (2).

4. The medical forceps according to claim 1, comprising two movable jaw parts (4, 6), respectively comprising at their proximal ends two linkage arms (16, 18) which are movably guided in an associated curved guide paths (12, 14) in at least one insert (8, 10; 46) in a longitudinal direction of the curved guide paths (12, 14), wherein the two linkage arms (16, 18) and the associated curved guide paths (12, 14) are curved oppositely to one another.

5. The medical forceps according to claim 4, wherein the two linkage arms (16, 18) and the associated curved guide paths (12, 14) are each curved in a plane, and the respective planes of curvature of the two linkage arms (16, 18) extend parallel to one another.

6. The medical forceps according to claim 1, wherein the at least one moveable jaw part (4, 6) and the linkage arm (16, 18) are electrically conducting.

7. The medical forceps according to claim 1, comprising two guide paths (12, 14) each formed as a groove in the insert (8, 10), and wherein each groove faces a longitudinal axis (X) of the forceps shank (2).

8. The medical forceps according to claim 7, comprising two inserts (8, 10) arranged such that their surfaces in which the guide paths (12, 14) are formed face one another.

9. The medical forceps according to claim 8, wherein the two inserts (8, 10) in assembled cross section have an outer contour which corresponds to a shape of an inner cross section of the forceps shank (2), and wherein the inserts are applied into the forceps shank (2) from the distal end.

10. The medical forceps according to claim 8, wherein the inserts (8, 10) have locking elements (20) which releasably engage with corresponding locking elements (22) on the forceps shank (2).

11. The medical forceps according to claim 7, comprising two inserts (8, 10) with an insulation element (24) arranged between the inserts.

12. The medical forceps according to claim 7, comprising two inserts (8, 10) applied into receptacles formed in an insulation element (40) at the distal end of the forceps shank (2).

13. The medical forceps according to claim 1, wherein the curved guide path (12, 14) is formed as a groove on an outer side of the insert (46) which is inserted into a receptacle arranged centrally at the distal end of the forceps shank (2) so that the curved guide path (12, 14) faces away from a longitudinal axis (X) of the forceps shank (2).

14. The medical forceps according to claim 13, comprising two curved guide paths (12, 14) on two opposing sides of the insert (46).

15. The medical forceps according to claim 1, wherein the curved guide path (12, 14) is formed in an insulation element.

* * * * *